United States Patent
Rampf et al.

(10) Patent No.: US 11,091,388 B2
(45) Date of Patent: Aug. 17, 2021

(54) GLASS CERAMIC HAVING SIO2 AS MAIN CRYSTAL PHASE

(71) Applicant: Ivoclar Vivadent AG, Schaan (LI)

(72) Inventors: Markus Rampf, Lachen (CH); Marc Dittmer, Feldkirch (AT); Christian Ritzberger, Grabs (CH); Marcel Schweiger, Chur (CH); Wolfram Höland, Schaan (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 16/454,747

(22) Filed: Jun. 27, 2019

(65) Prior Publication Data

US 2019/0315651 A1    Oct. 17, 2019

Related U.S. Application Data

(63) Continuation of application No. 15/310,823, filed as application No. PCT/EP2015/060765 on May 15, 2015, now Pat. No. 10,377,661.

(30) Foreign Application Priority Data

May 16, 2014    (EP) .................................... 14168719

(51) Int. Cl.

| C03C 10/00 | (2006.01) |
|---|---|
| C03C 3/087 | (2006.01) |
| C03C 3/097 | (2006.01) |
| A61K 6/833 | (2020.01) |
| A61K 6/836 | (2020.01) |
| A61C 13/00 | (2006.01) |
| A61C 13/08 | (2006.01) |
| A61C 13/083 | (2006.01) |
| C03B 19/06 | (2006.01) |
| C03B 32/00 | (2006.01) |
| C03C 3/112 | (2006.01) |
| C03C 4/00 | (2006.01) |

(52) U.S. Cl.
CPC ...... *C03C 10/0009* (2013.01); *A61C 13/0004* (2013.01); *A61C 13/081* (2013.01); *A61C 13/083* (2013.01); *A61K 6/833* (2020.01); *A61K 6/836* (2020.01); *C03B 19/063* (2013.01); *C03B 32/00* (2013.01); *C03C 3/087* (2013.01); *C03C 3/097* (2013.01); *C03C 3/112* (2013.01); *C03C 4/0021* (2013.01); *C03C 10/0027* (2013.01); *C03C 2204/00* (2013.01)

(58) Field of Classification Search
CPC .................................................. C03C 10/0009
USPC ............................................................ 501/4
See application file for complete search history.

(56) References Cited

U.S. PATENT DOCUMENTS

| 3,445,252 | A | ‡ | 5/1969 | MacDowell | ........ C03C 10/0027 501/4 |
|---|---|---|---|---|---|
| 3,804,608 | A | ‡ | 4/1974 | Gaskell | .................... C03C 10/00 65/33 |
| 4,011,091 | A | ‡ | 3/1977 | McCollister | ........ C03C 10/0027 501/4 |
| 4,050,946 | A | ‡ | 9/1977 | Li | ...................... C03C 10/0036 501/4 |
| 4,239,521 | A | ‡ | 12/1980 | Beall | ................... C03C 10/0027 65/114 |
| 4,755,488 | A | ‡ | 7/1988 | Nagashima | ........... C03C 21/002 501/4 |
| 5,057,018 | A | ‡ | 10/1991 | Bowen | ..................... A61C 5/00 106/35 |
| 5,173,453 | A | ‡ | 12/1992 | Beall | ................... C03C 10/0036 501/4 |
| 5,446,008 | A | ‡ | 8/1995 | Krolla | ................. C03C 10/0027 501/4 |
| 5,507,981 | A | ‡ | 4/1996 | Petticrew | ............... A61C 13/20 264/16 |
| 5,866,489 | A | ‡ | 2/1999 | Yamaguchi | ......... C03C 10/0027 501/4 |
| 6,174,827 | B1 | ‡ | 1/2001 | Goto | ................... C03C 10/0027 428/84 |
| 6,372,319 | B1 | ‡ | 4/2002 | Abe | ..................... C03C 10/0027 428/141 |
| 6,410,466 | B1 | ‡ | 6/2002 | Goto | ................... C03C 10/0027 501/4 |
| 6,426,311 | B1 | * | 7/2002 | Goto | ................... C03C 10/0027 428/846.4 |
| 7,601,446 | B2 | ‡ | 10/2009 | Ikenishi | .................. C03C 3/085 428/846.9 |

(Continued)

FOREIGN PATENT DOCUMENTS

| CA | 2252660 A1 | ‡ | 5/1999 |
|---|---|---|---|
| CA | 2252660 A1 | | 5/1999 |

(Continued)

OTHER PUBLICATIONS

International Preliminary Report on Patentability of PCT/EP2015/060765, dated Nov. 22, 2016, 7 pages.‡
Holand et al., "Properties of f3-Spodumere Solid Solution Glass-Ceramic NeoceramTM N-11 and the B-Quartz Solid-Solution Glass-Ceramics NeoceramTM N—O, Ceran@, and Robax@," Glass Ceramic Technology, 2nd Edition, Wiley, 2012, pp. 272-273.‡
Dittmer, Marc, "Glasses and glass-ceramics in the system of MgO—A1203—SiO2 with ZrO2 as nucleating agent," Dissertation, 2011, University of Jena.‡
Dittmer, Marc, "Glasses and glass-ceramics in the system of MgO—A1203—SiO2 with ZrO2 as nucleating agent," Dissertation, 2011, University of Jena.

(Continued)

*Primary Examiner* — Noah S Wiese
(74) *Attorney, Agent, or Firm* — Ann M. Knab; Thad McMurray

(57) ABSTRACT

Glass ceramics having $SiO_2$ as main crystal phase and precursors thereof are described which are characterized by very good mechanical and optical properties and in particular can be used as restoration material in dentistry.

20 Claims, No Drawings

(56) References Cited

U.S. PATENT DOCUMENTS

| | | | |
|---|---|---|---|
| 8,043,706 B2 * | 10/2011 | Goto | C03C 10/0045 428/426 |
| 2002/0137618 A1 ‡ | 9/2002 | Goto | C03C 10/0027 501/4 |
| 2003/0099062 A1 | 5/2003 | Kataoka et al. | |
| 2011/0030423 A1 ‡ | 2/2011 | Johannes | C03C 3/085 65/21 |
| 2012/0283086 A1 ‡ | 11/2012 | Schneider | C03C 1/10 501/27 |
| 2013/0149433 A1 ‡ | 6/2013 | Ehrt | A61K 6/0017 427/2 |
| 2019/0365515 A1 | 12/2019 | Dittmer et al. | |

FOREIGN PATENT DOCUMENTS

| | | | |
|---|---|---|---|
| EP | 0231773 | A1 ‡ | 8/1987 |
| EP | 0231773 | A1 | 8/1987 |
| JP | H10338540 | A ‡ | 12/1998 |
| JP | H10338540 | A | 12/1998 |
| JP | 2001288027 | A ‡ | 10/2001 |
| JP | 2001288027 | A | 10/2001 |

OTHER PUBLICATIONS

Höland et al., "Properties of ß-Spodumere Solid Solution Glass-Ceramic Neoceram™ N-11 and the ß-Quartz Solid-Solution Glass-Ceramics Neoceram™ N—O, Ceran®, and Robax®," Glass Ceramic Technology, 2nd Edition, Wiley, 2012, pp. 272-273.

Dittmer, Marc, "Crystallization and mechanical properties of MgO/Al2O3/SiO2/ZrO2 glass-ceramics with and without the addition of yttria," Journal Article, Solid State Sciences 13 (2011) 2146-2153, Elsevier Masson SAS.

Wikipedia, https://en.wikipedia.org/wiki/Inlays_and_onlays, "Inlays and onlays," Website article, Retrieved on Mar. 22, 2021, 8 pages.

Wikipedia, https://en.wikipedia.org/wiki/Bridge_(dentistry),"Bridge (dentistry)," Website article, Retrieved on Mar. 22, 2021, 9 pages.

\* cited by examiner
‡ imported from a related application

GLASS CERAMIC HAVING SIO2 AS MAIN CRYSTAL PHASE

CROSS-REFERENCE TO RELATED APPLICATIONS

This application is a continuation application of U.S. Ser. No. 15/310,823, filed on Nov. 14, 2016, which is a National Stage application of International patent application PCT/EP2015/060765 filed on May 15, 2015, which claims priority to European patent application No. 14168719.4 filed on May 16, 2014, all the disclosures of which are incorporated herein by reference in their entirety.

TECHNICAL FIELD

The invention relates to a glass ceramic having $SiO_2$ as main crystal phase which is suitable in particular for use in dentistry and preferably for the preparation of dental restorations, as well as to precursors to the preparation of the glass ceramic.

BACKGROUND

Glass ceramics with quartz-like crystals are already known from the state of the art. They are usually glass ceramics with so-called high quartz solid solution crystals. These crystals contain different additional ions in the $SiO_2$ framework silicate, which allow this particular type of crystal to have a metastable existence even at room temperature. If these ions were not contained in the glass ceramic, the high quartz formed at high temperatures in the glass ceramic would change into low quartz at 573° C. Höland and Beall describe that glass ceramics with crystals in the high quartz structure have the particular property of low thermal expansion or even of zero expansion within a large temperature range ("Glass-Ceramic Technology" $2^{nd}$ edition, Wiley, 2012, 272-273). For such glass ceramics, linear coefficients of thermal expansion (CTE) of less than $1.5 \cdot 10^{-6}$ $K^{-1}$ (within the temperature range of 20-700° C.) are usually measured. Even glass ceramics with a negative coefficient of expansion can be provided with the aid of the high quartz structure.

Further, lithium disilicate glass ceramics are known from EP 916 625, which contain lithium disilicate as main crystal phase and, because of their high translucence and very good mechanical properties, are used particularly in the dental field and primarily for the preparation of crowns and bridges.

SUMMARY

The object of the invention is to provide a glass ceramic which, in addition to a high strength and very good optical properties, is also characterized by a high coefficient of thermal expansion. The glass ceramic should further be easy to process, in particular by machining, to form dental restorations and thus be suitable in an excellent manner as restorative dental material. It would be desirable if the glass ceramic could also be given the desired shape by means of hot pressing.

DETAILED DESCRIPTION

The glass ceramic according to the invention is characterized in that it comprises the following components

| Component | wt.-% |
| --- | --- |
| $SiO_2$ | 58.0 to 92.0 |
| $Li_2O$ | 2.0 to 10.0 | and comprises $SiO_2$ as main crystal phase.

This glass ceramic surprisingly displays an advantageous combination of mechanical and optical properties desirable for a restorative dental material, and it can also be given the desired shape in a manner desirable for a dental material.

The glass ceramic according to the invention contains in particular 60.0 to 90.0, preferably 70.0 to 83.0 wt.-% and particularly preferably 73.0 to 81.0 wt.-% $SiO_2$.

It is further preferred that the glass ceramic contains 2.8 to 9.0, in particular 5.0 to 9.0 and particularly preferably 5.0 to 7.8 wt.-% $Li_2O$. $Li_2O$ serves to improve the meltability of the starting glasses. Further, it also promotes the mobility of the ions in the glass matrix, and it is assumed that this has a positive effect on the crystallization of some crystal phases, e.g. of low quartz and lithium silicate.

It is also preferred that the glass ceramic, in addition to $Li_2O$, contains further alkali metal oxide $Me^I_2O$ in an amount of from 0 to 13.0, in particular 1.0 to 13.0 and particularly preferably 2.0 to 13.0 wt.-%. The term "further alkali metal oxide $Me^I_2O$" refers to alkali metal oxide with the exception of $Li_2O$, wherein this $Me^I_2O$ is selected in particular from $Na_2O$, $K_2O$, $Rb_2O$ and/or $Cs_2O$. The glass ceramic particularly preferably contains at least one and in particular all of the following further alkali metal oxides $Me^I_2O$ in the amounts specified:

| Component | wt.-% |
| --- | --- |
| $Na_2O$ | 0 to 3.0 |
| $K_2O$ | 0 to 5.0 |
| $Rb_2O$ | 0 to 7.0 |
| $Cs_2O$ | 0 to 13.0. |

In a particularly preferred embodiment, the glass ceramic according to the invention contains 1.0 to 4.0 wt.-% $K_2O$.

In addition, it is preferred that the glass ceramic contains 0 to 11.0 and in particular 1.0 to 7.0 wt.-% oxide of divalent elements $Me^{II}O$, wherein this oxide $Me^{II}O$ is selected in particular from MgO, CaO, SrO and/or ZnO. The glass ceramic particularly preferably contains at least one and in particular all of the following oxides of divalent elements $Me^{II}O$ in the quantities specified:

| Component | wt.-% |
| --- | --- |
| CaO | 0 to 4.5 |
| MgO | 0 to 7.0 |
| SrO | 0 to 5.0 |
| ZnO | 0 to 4.0. |

In a particularly preferred embodiment, the glass ceramic according to the invention contains 1.0 to 7.0, and in particular 1.0 to 2.0 wt.-% MgO.

Further, a glass ceramic is preferred which contains 0 to 10.0 and in particular 2.0 to 9.0 wt.-% oxide of trivalent elements $Me^{III}_2O_3$, wherein this $Me^{III}_2O_3$ is selected in particular from $Al_2O_3$, $B_2O_3$, $Y_2O_3$, $La_2O_3$, $Ga_2O_3$ and/or $In_2O_3$. The glass ceramic particularly preferably contains at least one and in particular all of the following oxides of trivalent elements $Me^{III}_2O_3$ in the amounts specified:

| Component | wt.-% |
|---|---|
| $Al_2O_3$ | 0 to 8.0 |
| $Y_2O_3$ | 0 to 3.0 |
| $B_2O_3$ | 0 to 5.0 |
| $Ga_2O_3$ | 0 to 2.0 |
| $In_2O_3$ | 0 to 1.0 |
| $La_2O_3$ | 0 to 2.0. |

In a particularly preferred embodiment, the glass ceramic according to the invention contains 2.0 to 8.0 wt.-% $Al_2O_3$.

Furthermore, a glass ceramic is preferred which contains further oxide of tetravalent elements $Me^{IV}O_2$ in an amount of from 0 to 21.0 wt.-%. The term "further oxide of tetravalent elements $Me^{IV}O_2$" refers to tetravalent oxides with the exception of $SiO_2$, wherein this $Me^{IV}O_2$ is selected in particular from $ZrO_2$, $GeO_2$, $CeO_2$, $TiO_2$ and/or $SnO_2$. The glass ceramic particularly preferably contains at least one and in particular all of the following further oxides of tetravalent elements $Me^{IV}O_2$ in the amounts specified:

| Component | wt.-% |
|---|---|
| $ZrO_2$ | 0 to 11.0 |
| $TiO_2$ | 0 to 5.0 |
| $SnO_2$ | 0 to 3.0 |
| $GeO_2$ | 0 to 21.0 |
| $CeO_2$ | 0 to 3.0. |

In a further preferred embodiment, the glass ceramic contains 0 to 7.0, in particular 0 to 6.5, particularly preferably 1.0 to 6.5 and quite particularly preferably 2.0 to 6.5 wt.-% $P_2O_5$. $P_2O_5$ can act as nucleating agent. However, the presence of a nucleating agent is not absolutely necessary for the formation of $SiO_2$ as main crystal phase.

Moreover, a glass ceramic is preferred which contains further oxide of pentavalent elements $Me^V_2O_5$ in an amount of from 0 to 6.0 and in particular 0 to 5.0 wt.-%. The term "further oxide of pentavalent elements $Me^V_2O_5$" refers to pentavalent oxides with the exception of $P_2O_5$, wherein this $Me^V_2O_5$ is selected in particular from $V_2O_5$, $Ta_2O_5$ and/or $Nb_2O_5$. The glass ceramic particularly preferably contains at least one and in particular all of the following further oxides of pentavalent elements $Me^V_2O_5$ in the amounts specified:

| Component | wt.-% |
|---|---|
| $V_2O_5$ | 0 to 6.0 |
| $Ta_2O_5$ | 0 to 5.0 |
| $Nb_2O_5$ | 0 to 5.0. |

A glass ceramic is also preferred which contains 0 to 6.0 wt.-% oxide of hexavalent elements $Me^{VI}O_3$, wherein this $Me^{VI}O_3$ is selected in particular from $WO_3$ and/or $MoO_3$. The glass ceramic particularly preferably contains at least one and in particular all of the following oxides $Me^{VI}O_3$ in the amounts specified:

| Component | wt.-% |
|---|---|
| $WO_3$ | 0 to 6.0 |
| $MoO_3$ | 0 to 5.0. |

In addition, a glass ceramic is preferred which contains 0 to 5.0 and in particular 0 to 1.0 wt.-% fluorine.

A glass ceramic is particularly preferred which contains at least one and preferably all of the following components in the amounts specified:

| Component | wt.-% |
|---|---|
| $SiO_2$ | 58.0 to 92.0 |
| $Li_2O$ | 2.0 to 10.0 |
| $Me^I_2O$ | 0 to 13.0 |
| $Me^{II}O$ | 0 to 11.0 |
| $Me^{III}_2O_3$ | 0 to 10.0 |
| $Me^{IV}O_2$ | 0 to 21.0 |
| $P_2O_5$ | 0 to 7.0 |
| $Me^V_2O_5$ | 0 to 6.0 |
| $Me^{VI}O_3$ | 0 to 6.0 |
| fluorine | 0 to 5.0, | wherein $Me^I_2O$, $Me^{II}O$, $Me^{III}_2O_3$, $Me^{IV}O_2$, $Me^V_2O_5$ and $Me^{VI}O_3$ have the above-specified meaning.

In a further particularly preferred embodiment, the glass ceramic contains at least one and preferably all of the following components:

| Component | wt.-% |
|---|---|
| $SiO_2$ | 60.0 to 90.0 |
| $Li_2O$ | 2.8 to 9.0 |
| $Na_2O$ | 0 to 3.0 |
| $K_2O$ | 0 to 5.0 |
| $Rb_2O$ | 0 to 7.0 |
| $Cs_2O$ | 0 to 13.0 |
| CaO | 0 to 4.5 |
| MgO | 0 to 7.0 |
| SrO | 0 to 5.0 |
| ZnO | 0 to 4.0 |
| $Al_2O_3$ | 0 to 8.0 |
| $Y_2O_3$ | 0 to 3.0 |
| $B_2O_3$ | 0 to 5.0 |
| $Ga_2O_3$ | 0 to 2.0 |
| $In_2O_3$ | 0 to 1.0 |
| $La_2O_3$ | 0 to 2.0 |
| $ZrO_2$ | 0 to 11.0 |
| $TiO_2$ | 0 to 5.0 |
| $SnO_2$ | 0 to 3.0 |
| $GeO_2$ | 0 to 21.0 |
| $CeO_2$ | 0 to 3.0 |
| $P_2O_5$ | 0 to 6.5 |
| $Ta_2O_5$ | 0 to 5.0 |
| $Nb_2O_5$ | 0 to 5.0 |
| $V_2O_5$ | 0 to 6.0 |
| $WO_3$ | 0 to 6.0 |
| $MoO_3$ | 0 to 5.0 |
| fluorine | 0 to 1.0. |

Some of the above-mentioned components can serve as colorants and/or fluorescent agents. The glass ceramic according to the invention can in addition also contain further colorants and/or fluorescent agents, which can be selected in particular from inorganic pigments and/or oxides of d- and f-elements, such as the oxides of Sc, Mn, Fe, Co, Pr, Nd, Tb, Er, Dy, Gd, Eu and Yb. Metal colloids, e.g. of Ag, Au and Pd, which can in addition also act as nucleating agents, can also be used as further colorants. These metal colloids can be formed e.g. by reduction of corresponding oxides, chlorides or nitrates during the melting and crystallization processes.

The properties of the glass ceramic are substantially influenced by the main crystal phase. The glass ceramic according to the invention contains $SiO_2$ as main crystal phase. In a preferred embodiment, the glass ceramic according to the invention contains low quartz, cristobalite or a mixture thereof, preferably low quartz or cristobalite and particularly preferably low quartz, as main crystal phase.

The term "main crystal phase" refers to the crystal phase which has the highest proportion by mass out of all the crystal phases present in the glass ceramic. The masses of the crystal phases are in particular determined using the Rietveld method. A suitable method for the quantitative analysis of the crystal phases using the Rietveld method is described e.g. in M. Dittmer's doctoral thesis "Gläser and Glaskeramiken im System MgO—$Al_2O_3$—$SiO_2$ mit $ZrO_2$ als Keimbildner" [Glasses and glass ceramics in the MgO—$Al_2O_3$—$SiO_2$ system with $ZrO_2$ as nucleating agent], University of Jena 2011.

It is further preferred that the glass ceramic according to the invention contains 5.0 to 50.0 and in particular 10.0 to 30.0 wt.-% $SiO_2$ as crystal phase, in particular in the form of low quartz, cristobalite or mixtures thereof.

The glass ceramic according to the invention can contain, in addition to $SiO_2$ as main crystal phase, also further crystal phases, such as in particular lithium phosphate and/or lithium silicate. Still further nanoscale phases in amorphous or crystalline form can likewise also be present in the glass ceramic according to the invention.

It is preferred that the glass ceramic according to the invention comprises 5.0 to 30.0 and in particular 10.0 to 25.0 wt.-% lithium disilicate.

The type and quantity of crystal phases formed can be controlled in particular by the composition of the starting glass as well as the heat treatment which is used to prepare the glass ceramic from the starting glass. The examples illustrate this by varying the composition and the heat treatment applied.

The glass ceramic according to the invention has a coefficient of thermal expansion CTE (measured in the range of from 100 to 500° C.) of in particular at least $5.0 \cdot 10^{-6}$ $K^{-1}$, preferably 10.0 to $20.0 \cdot 10^{-6}$ $K^{-1}$ and particularly preferably 13.0 to $18.0 \cdot 10^{-6}$ $K^{-1}$. The CTE is determined according to ISO 6872 (2008).

The glass ceramic according to the invention is characterized by a very good chemical stability. To determine the chemical stability, the glass ceramic was tested according to ISO standard 6872 (2008) by determining the mass loss during storage in aqueous acetic acid. The glass ceramic according to the invention displayed a mass loss of preferably less than 30 µg/$cm^2$.

Furthermore, the glass ceramic according to the invention is characterized in particular by mechanical properties which allow a particularly simple and quick machining to bring the glass ceramic e.g. into the shape of a dental restoration.

The glass ceramic has a biaxial breaking strength of preferably at least 200 MPa and particularly preferably 200 to 500 MPa. The biaxial breaking strength was determined according to ISO 6872 (2008) (piston-on-three-balls test).

The translucence of the glass ceramic was determined in the form of the contrast value (CR value) according to British Standard BS 5612 and it was preferably 35 to 80.

The invention likewise relates to precursors with a corresponding composition from which the glass ceramic according to the invention can be prepared by heat treatment. These precursors are a starting glass with corresponding composition and a starting glass with nuclei with corresponding composition. The term "corresponding composition" means that these precursors contain the same components in the same amounts as the glass ceramic, wherein the components with the exception of fluorine are calculated as oxides, as is customary for glasses and glass ceramics.

The invention therefore likewise relates to a starting glass which contains the components of the glass ceramic according to the invention.

The starting glass according to the invention therefore contains as components

| Component | wt.-% |
|---|---|
| $SiO_2$ | 58.0 to 92.0 |
| $Li_2O$ | 2.0 to 10.0. |

Further, the starting glass can also contain other components, such as are specified above for the glass ceramic according to the invention. All those embodiments which are also specified as preferred for the components of the glass ceramic according to the invention are preferred for the components of the starting glass.

The invention likewise relates to a starting glass which contains nuclei for the crystallization of $SiO_2$ and in particular of low quartz and/or cristobalite and preferably of low quartz.

By heat treatment of the starting glass, the starting glass with nuclei can be produced first, which can for its part be converted into the glass ceramic according to the invention having $SiO_2$ as main crystal phase by further heat treatment.

The preparation of the starting glass is carried out in particular in such a way that a mixture of suitable starting materials, such as carbonates, oxides and phosphates, is melted at temperatures of in particular from 1500 to 1800° C. for 0.5 to 10 h. To achieve a particularly high homogeneity, the obtained glass melt is poured into water in order to form a glass granulate, and the obtained granulate is then melted again.

The melt can then be poured into moulds, e.g. steel or graphite moulds, in order to produce blanks of the starting glass, so-called solid glass blanks or monolithic blanks. These monolithic blanks are usually stress-relieved first, e.g. by keeping them at 450 to 600° C. for 5 to 120 min. This stress relief in the specified temperature range usually leads to the formation of nuclei for the crystallization of $SiO_2$ crystal phase and in particular of low quartz crystal phase.

It is likewise possible to put the melt into water again in order to prepare a frit, i.e. a granulate. This frit can be pressed, after grinding and, optionally, addition of further components, such as binders and/or colorants and fluorescent agents, to form a blank, a so-called powder compact.

Finally, the starting glass can also be processed to form a powder after the production of a glass frit.

The starting glass with nuclei can then be produced from the starting glass by heat treatment. This is also called nucleation process.

The invention is therefore likewise directed towards a method for the preparation of the starting glass with nuclei for the crystallization of $SiO_2$, in particular of low quartz, in which the starting glass is subjected to a heat treatment at a temperature of from 450 to 600° C. and in particular 500 to 550° C. for a period of in particular from 5 to 120 min and preferably 10 to 40 min.

The glass ceramic according to the invention can then be formed from the starting glass with nuclei by heat treatment.

The invention is therefore likewise directed towards a method for the preparation of the glass ceramic according to the invention, in which the starting glass, in particular the starting glass with nuclei, is subjected to at least one heat treatment at a temperature of from 700 to 950° C. for a period of in particular from 5 to 40 min and preferably 10 to 30 min.

The starting glass or the starting glass with nuclei can be subjected to the at least one heat treatment e.g. in the form of a solid glass blank or a powder compact.

The at least one heat treatment carried out in the method according to the invention can also take place during a hot pressing, in particular of a solid glass blank, or during a sintering-on, in particular of a powder.

The invention in a preferred embodiment thus relates to a method for the preparation of the glass ceramic according to the invention, in which (a) powder of the starting glass, optionally after the addition of further components, such as pressing aids, colorants and/or fluorescent agents, is pressed to form a powder compact, and (b) the powder compact is subjected to a heat treatment at a temperature of from 700 to 950° C. for a period of in particular from 5 to 40 min.

In a further preferred embodiment the invention relates to a method for the preparation of the glass ceramic according to the invention, in which (a') melt of the starting glass is shaped to form a glass blank, in particular by pouring it into a mould, and (b') the glass blank is subjected to a heat treatment at a temperature of from 700 to 900° C. for a period of in particular from 5 to 40 min.

In both preferred embodiments of the method according to the invention a further above-described nucleation can be carried out before the heat treatment in step (b) or (b').

The glass ceramics according to the invention and the glasses according to the invention are present in particular in the form of powders, granulates or blanks in any form or size, e.g. monolithic blanks, such as platelets, cuboids or cylinders, or powder compacts, in unsintered, partly sintered or densely-sintered form. They can easily be further processed in these forms, e.g. to form dental restorations. They can, however, also be present in the form of dental restorations, such as inlays, onlays, crowns, veneers, facets or abutments.

Dental restorations, such as bridges, inlays, onlays, crowns, veneers, facets or abutments, can be prepared from the glass ceramics according to the invention and the glasses according to the invention. The invention therefore relates to their use as dental material and in particular to their use for the preparation of dental restorations. It is preferred that the glass ceramic or the glass is given the shape of the desired dental restoration by pressing or machining.

The pressing is usually carried out under increased pressure and at increased temperature. It is preferred that the pressing is carried out at a temperature of from 700 to 1200° C. It is further preferred to carry out the pressing at a pressure of from 10 to 30 bar. During pressing, the desired shape change is achieved by viscous flow of the material used. The starting glass according to the invention and the starting glass with nuclei according to the invention as well as preferably the glass ceramic according to the invention can be used for the pressing. The glasses and glass ceramics according to the invention can be used in particular in the form of blanks in any form or size, e.g. solid blanks or powder compacts, e.g. in unsintered, partly sintered or densely-sintered form.

The machining is usually carried out by material removal processes and in particular by milling and/or grinding. It is particularly preferred that the machining is carried out as part of a CAD/CAM method. The starting glass according to the invention, the starting glass with nuclei according to the invention as well as the glass ceramic according to the invention can be used for the machining. The glasses and glass ceramics according to the invention can be used in particular in the form of blanks, e.g. solid blanks or powder compacts, e.g. in unsintered, partly sintered or densely-sintered form. The glass ceramic according to the invention is preferably used for the machining. The glass ceramic according to the invention can also be used in a not yet fully crystallized form which was produced by heat treatment at a lower temperature. This has the advantage that an easier machining and thus the use of simpler equipment for the machining is possible. After the machining of such a partly-crystallized material, the latter is usually subjected to a further heat treatment in order to cause a further crystallization of $SiO_2$ as crystal phase.

However, the glass ceramics according to the invention and the glasses according to the invention are also suitable as coating material of e.g. ceramics, glass ceramics and metals. The invention is therefore likewise directed towards the use of the glasses according to the invention or the glass ceramics according to the invention for coating of in particular ceramics, glass ceramics and metals.

The invention also relates to a method for coating of ceramics, glass ceramics and metals, in which glass ceramic according to the invention or glass according to the invention is applied to the ceramic, the glass ceramic or the metal and exposed to a temperature of at least 600° C.

This can take place in particular by sintering-on and preferably by pressing-on. With sintering-on, the glass ceramic or the glass is applied to the material to be coated, such as ceramic, glass ceramic or metal, in the usual way, e.g. as powder, and then sintered. With the preferred pressing-on, glass ceramic according to the invention or glass according to the invention is pressed on, e.g. in the form of powder compacts or monolithic blanks, at an increased temperature of e.g. from 700 to 1200° C., accompanied by the application of pressure, e.g. 10 to 30 bar. The methods described in EP 231 773 and the press furnace disclosed there can be used in particular for this. Suitable commercial furnaces are the furnaces of the Programat type from Ivoclar Vivadent AG, Liechtenstein.

Because of the above-described properties of the glass ceramics according to the invention and the glasses according to the invention, these are suitable in particular for use in dentistry. A subject of the invention is therefore also the use of the glass ceramics according to the invention or the glasses according to the invention as dental material and in particular for the preparation of dental restorations or as coating material for dental restorations, such as crowns, bridges and abutments.

The invention therefore also relates to a method for the preparation of a dental restoration, in particular bridge, inlay, onlay, veneer, abutment, partial crown, crown or facet, in which the glass ceramic according to the invention or the starting glass according to the invention is given the shape of the desired dental restoration by pressing, sintering or machining, in particular as part of a CAD/CAM method.

The invention is described in more detail below with reference to non-limiting examples.

EXAMPLES

Examples 1 to 35—Composition and Crystal Phases

A total of 35 glasses and glass ceramics having the composition given in Table I were prepared by melting corresponding starting glasses, optionally nucleation or stress relief, and then heat treatment for the crystallization.

The following meanings apply in Table 1:

| | |
|---|---|
| $T_g$ | glass transition temperature, determined by means of DSC |
| $T_s$ and $t_s$ | temperature and time used for melting the starting glass |
| $T_{Kb}$ and $t_{Kb}$ | temperature and time used for nucleation or stress relief of the starting glass |
| $T_c$ and $t_c$ | temperature and time used for crystallization of solid glass blocks |
| $T_{Sinter}$ and $t_{Sinter}$ | temperature and time used for crystallization of powder compacts |
| $T_{Press}$ and $t_{Press}$ | temperature and time used for crystallization of solid glass blocks by hot pressing |
| CR value | contrast value of the glass ceramic according to British Standard BS 5612 determined using: apparatus: CM-3700d spectrometer (Konica-Minolta) measurement parameters: measurement area: 7 mm × 5 mm type of measurement: reflectance/reflection measurement range: 400 nm-700 nm sample size: diameter: 15-20 mm thickness: 2 mm +− 0.025 mm plane parallelism: +−0.05 mm surface roughness: about 18 µm. |
| CTE | coefficient of thermal expansion of the glass ceramic according to ISO 6872 (2008), measured in the range of from 100 to 500° C. |

In Examples 1 to 35 the starting glasses were first melted on a scale of 100 to 200 g from usual raw materials at the temperature $T_S$ for a period $t_S$. Glass frits were prepared by pouring the melted starting glasses into water. For the further processing of the glass frits, the three method variants A), B) and C) specified below were used:

A) Solid Glass Blocks

In examples for which $T_C$ and $t_C$ are specified in Table 1 (Examples 3-5, 7-12, 14, 16-24 and 26-35), the glass ceramics were prepared from solid glass blocks. For this, the obtained glass frits were melted again at the temperature $T_S$ for a period $t_S$. The obtained melts of the starting glass were then poured into a graphite mould in order to produce solid glass blocks. These glass monoliths were then usually stress-relieved at the temperature $T_{Kb}$ for a period $t_{Kb}$, whereby nucleation could take place. The nucleated starting glasses were then heated to a temperature $T_C$ for a period $t_C$. Glass ceramics according to the invention comprising $SiO_2$ as main crystal phase were thereby formed, as could be established by X-ray diffraction tests at room temperature.

It is assumed that in this method variant a volume crystallization of the $SiO_2$ crystal phase has taken place.

B) Powder Compacts

In examples for which $T_{Sinter}$ and $t_{Sinter}$ are specified in Table 1 (1, 2, 6, 15 and 25), the glass ceramics were prepared from powder compacts. For this, the obtained glass frits were ground in a zirconium oxide mill to a particle size of <90 µm. About 4 g of these powders were then pressed to form cylindrical blanks and sintered in a sinter furnace (Programat® from Ivoclar Vivadent AG) at a temperature $T_{Sinter}$ and a holding time of $t_{Sinter}$ to form dense glass ceramic bodies. Glass ceramics according to the invention comprising $SiO_2$ as main crystal phase were formed by the sintering, as could be established by X-ray diffraction tests at room temperature.

It is assumed that in this method variant a surface crystallization of the $SiO_2$ crystal phase has taken place.

C) Hot Pressing of Solid Glass Blocks

In Example 13, for which $T_{Press}$ and $t_{Press}$ are specified, the glass ceramic was prepared by hot pressing of solid glass blocks.

For this, the obtained glass frit was melted again at the temperature $T_S$ for a period $t_S$. The obtained melt of the starting glass was then poured into a pre-heated steel mould in order to produce rods. These monolithic glass rods were then stress-relieved at a temperature $T_{Kb}$ for a period $t_{Kb}$, whereby nucleation could take place. The rods were then sawn into blocks with a mass of about 4 to 6 g. These solid glass blocks were then pressed to form a shaped body in a hot-pressing furnace at the temperature $T_{press}$ and for a holding time of $t_{press}$. Glass ceramic according to the invention comprising $SiO_2$ as main crystal phase was formed by the hot pressing, as could be established by X-ray diffraction tests of the formed shaped body at room temperature.

The glass ceramic blocks produced according to Examples 1 to 12 and 14 to 35 were machined in a CAD/CAM unit to form desired test pieces according to dental standard and to form dental restorations, such as crowns. For this, the crystallized blocks were provided with a suitable holder and then given the desired shape in an inLab MC XL grinding unit from Sirona Dental GmbH, Austria.

For the glass ceramic according to Example 1, the colour values (L, a, b) were additionally determined according to DIN5033 and DIN6174 as follows:

L: 90.68
a: −0.54
b: 4.82

The examination of the chemical stability according to ISO 6872 (2008) of the glass ceramic according to Example 1 yielded an acid solubility of only 5 µg/cm².

Further, glass ceramic blocks obtained according to Example 1 were provided with appropriate holders, and test pieces for determining the biaxial strength were ground out of them with an inLab grinding unit from Sirona Dental GmbH. The test pieces were polished to 15 µm and then the biaxial strength was determined without further thermal treatment. The average strength of the thus-prepared test pieces was 247 MPa.

TABLE I

| | Example No. | | | | | |
|---|---|---|---|---|---|---|
| Composition | 1 wt.-% | 2 wt.-% | 3 wt.-% | 4 wt.-% | 5 wt.-% | 6 wt.-% |
| $SiO_2$ | 80.1 | 60.0 | 77.5 | 77.1 | 80.1 | 80.1 |
| $Li_2O$ | 6.7 | 2.8 | 7.3 | 7.6 | 6.7 | 6.7 |
| $Na_2O$ | — | 1.0 | — | — | — | — |
| $K_2O$ | 3.0 | 3.3 | 3.2 | 2.1 | 3.0 | 3.0 |
| $Cs_2O$ | — | — | — | — | — | — |
| $Rb_2O$ | — | — | — | — | — | — |
| MgO | 1.5 | 3.0 | 1.7 | 1.6 | — | 4.3 |

TABLE I-continued

| Composition | | | | | | |
|---|---|---|---|---|---|---|
| CaO | 2.8 | 2.5 | — | — | 4.3 | — |
| SrO | — | — | — | — | — | — |
| ZnO | — | — | — | — | — | — |
| $Al_2O_3$ | 3.1 | 3.0 | 3.4 | 5.1 | 3.1 | 3.1 |
| $La_2O_3$ | — | — | — | 0.8 | — | — |
| $B_2O_3$ | — | — | 3.7 | — | — | — |
| $Y_2O_3$ | — | — | — | 0.8 | — | — |
| $Ga_2O_3$ | — | — | — | 0.8 | — | — |
| $In_2O_3$ | — | — | — | 0.5 | — | — |
| $ZrO_2$ | — | — | — | — | — | — |
| $TiO_2$ | — | — | — | — | — | — |
| $SnO_2$ | | | | | | |
| $CeO_2$ | — | — | — | — | — | — |
| $GeO_2$ | — | 20.3 | — | — | — | — |
| $V_2O_5$ | — | — | — | — | — | — |
| $Ta_2O_5$ | | | | | | |
| $Nb_2O_5$ | | | | | | |
| $P_2O_5$ | 2.8 | 4.1 | 3.2 | 3.6 | 2.8 | 2.8 |
| $MoO_3$ | | | | | | |
| $WO_3$ | — | — | — | — | — | — |
| F | | | | | | |
| $T_g$/° C. | 493 | 500 | 488 | | 501 | 505 |
| $T_s$/° C., $t_s$/min | 1650, 150 | 1680, 60 | 1630, 150 | 1650, 60 | 1600, 60 | 1600, 60 |
| $T_{Kb}$/° C., $t_{Kb}$/min | | | 500, 10 | 540, 10 | 520, 90 | 540, 30 |
| $T_c$/° C., $t_c$/min | | | 780, 15 | 800, 10 | 800, 30 | |
| $T_{Sinter}$/° C., $t_{Sinter}$/min | 860, 10 | 870, 15 | | | | 910, 10 |
| $T_{Press}$/° C., $t_{Press}$/min | | | | | | |
| Main crystal phase | low quartz | low quartz | low quartz | low quartz | low quartz | low quartz |
| Further crystal phases | $Li_3PO_4$ | $Li_3PO_4$; cristobalite; diopside | $Li_2Si_2O_5$; $Li_3PO_4$ | $Li_2Si_2O_5$; $Li_3PO_4$; cristobalite | $Li_2Si_2O_5$; $Li_3PO_4$ | $Li_3PO_4$; cristobalite |
| CR value | | 57.3 | | 68 | | |
| CTE/$10^{-6}K^{-1}$ (100-500° C.) | | | 16.8 | | 16 | 15.9 |

| | Example No. | | | | | |
|---|---|---|---|---|---|---|
| Composition | 7 wt.-% | 8 wt.-% | 9 wt.-% | 10 wt.-% | 11 wt.-% | 12 wt.-% |
| $SiO_2$ | 80.1 | 75.2 | 77.8 | 75.1 | 75.4 | 77.9 |
| $Li_2O$ | 6.7 | 6.7 | 6.7 | 7.1 | 7.6 | 7.7 |
| $Na_2O$ | — | — | — | — | — | — |
| $K_2O$ | 3.0 | — | — | 3.1 | 2.1 | 2.1 |
| $Cs_2O$ | — | 9.2 | — | — | — | — |
| $Rb_2O$ | — | — | 6.6 | — | — | — |
| MgO | — | 3.3 | 3.3 | 1.6 | 1.6 | 1.6 |
| CaO | — | — | — | 1.7 | — | — |
| SrO | 4.3 | — | — | — | — | — |
| ZnO | — | — | — | — | — | — |
| $Al_2O_3$ | 3.1 | 2.8 | 2.8 | 3.3 | 5.1 | 5.2 |
| $La_2O_3$ | — | — | — | — | — | — |
| $B_2O_3$ | — | — | — | — | — | — |
| $Y_2O_3$ | — | — | — | — | — | 1.9 |
| $Ga_2O_3$ | — | — | — | — | — | — |
| $In_2O_3$ | — | — | — | — | — | — |
| $ZrO_2$ | — | — | — | — | — | — |
| $TiO_2$ | — | — | — | — | — | — |
| $SnO_2$ | | | | | | |
| $CeO_2$ | — | — | — | — | — | — |
| $GeO_2$ | — | — | — | — | — | — |
| $V_2O_5$ | — | — | — | — | 4.6 | — |
| $Ta_2O_5$ | | | | | | |
| $Nb_2O_5$ | | | | | | |
| $P_2O_5$ | 2.8 | 2.8 | 2.8 | 3.1 | 3.6 | 3.6 |
| $MoO_3$ | | | | | | |
| $WO_3$ | — | — | — | 5.0 | — | — |
| F | | | | | | |
| $T_g$/° C. | 518 | 523 | 516 | 501 | 573 | 498 |
| $T_s$/° C., $t_s$/min | 1600, 60 | 1600, 60 | 1600, 60 | 1650, 60 | 1650, 60 | 1650, 60 |
| $T_{Kb}$/° C., $t_{Kb}$/min | 550, 40 | 530, 80 | 520, 120 | 520, 10 | 590, 10 | 520, 10 |
| $T_c$/° C., $t_c$/min | 820, 10 | 800, 30 | 850, 15 | 780, 15 | 780, 15 | 800, 15 |
| $T_{Sinter}$/° C., $t_{Sinter}$/min | | | | | | |
| $T_{Press}$/° C., $t_{Press}$/min | | | | | | |
| Main crystal phase | low quartz | low quartz | low quartz | low quartz | low quartz | low quartz |
| Further crystal phases | $Li_2Si_2O_5$; cristobalite; $Li_3PO_4$; $CaAl_{10}SiO_{22}$ | $Li_2Si_2O_5$; $Cs_{0809}AlSi_5O_{12}$; $Li_3PO_4$ | $Li_2Si_2O_5$; $Li_3PO_4$ | $Li_2Si_2O_5$; $CaWO_4$; $Li_3PO_4$ | $Li_2Si_2O_5$; $Li_3PO_4$ | $Li_3PO_4$; cristobalite, $Li_2Si_2O_5$ |

TABLE I-continued

| | | | | | | |
|---|---|---|---|---|---|---|
| CR value | | 91.6 | | 90.6 | | |
| CTE/$10^{-6}$K$^{-1}$ (100-500° C.) | 15.7 | 16.4 | 14.5 | 15.6 | 16.9 | |

| | Example No. | | | | | |
|---|---|---|---|---|---|---|
| Composition | 13 wt.-% | 14 wt.-% | 15 wt.-% | 16 wt.-% | 17 wt.-% | 18 wt.-% |
| SiO$_2$ | 79.2 | 77.6 | 79.6 | 78.4 | 79.0 | 90.0 |
| Li$_2$O | 6.7 | 6.6 | 7.8 | 5.9 | 6.8 | 6.7 |
| Na$_2$O | — | — | — | — | — | — |
| K$_2$O | 3.0 | 2.9 | 3.5 | 2.7 | 3.0 | 1.3 |
| Cs$_2$O | — | — | — | — | — | — |
| Rb$_2$O | — | — | — | — | — | — |
| MgO | 1.5 | 1.4 | 1.9 | 1.3 | 1.5 | 1.0 |
| CaO | 2.8 | 2.7 | 3.4 | 2.5 | 2.7 | — |
| SrO | 1.0 | 1.0 | — | — | — | — |
| ZnO | — | — | — | — | — | — |
| Al$_2$O$_3$ | 3.0 | 3.0 | 3.8 | 2.7 | 3.2 | — |
| La$_2$O$_3$ | — | — | — | — | — | — |
| B$_2$O$_3$ | — | — | — | — | — | — |
| Y$_2$O$_3$ | — | — | — | — | — | — |
| Ga$_2$O$_3$ | — | — | — | — | — | — |
| In$_2$O$_3$ | — | — | — | — | — | — |
| ZrO$_2$ | — | — | — | — | — | — |
| TiO$_2$ | — | — | — | — | — | — |
| SnO$_2$ | | | | | | |
| CeO$_2$ | — | 2.0 | — | — | — | — |
| GeO$_2$ | — | — | — | — | — | — |
| V$_2$O$_5$ | — | 0.1 | — | — | — | — |
| Ta$_2$O$_5$ | | | | | | |
| Nb$_2$O$_5$ | | | | | | |
| P$_2$O$_5$ | 2.8 | 2.7 | — | 6.5 | 3.0 | 1.0 |
| MoO$_3$ | | | | | | |
| WO$_3$ | — | — | — | — | — | — |
| F | — | — | — | — | 0.8 | — |
| T$_g$/° C. | | | 501 | 582 | 440 | 470 |
| T$_s$/° C., t$_s$/min | 1650, 50 | 1600, 150 | 1650, 60 | 1640, 60 | 1650, 60 | 1700, 60 |
| T$_{Kb}$/° C., t$_{Kb}$/min | 510, 10 | 510, 10 | | 600, 10 | 460, 10 | 480, 10 |
| T$_c$/° C., t$_c$/min | | 780, 10 | | 890, 10 | 780, 30 | 880, 10 |
| T$_{Sinter}$/° C., t$_{Sinter}$/min | | | 870, 15 | | | |
| T$_{Press}$/° C., t$_{Press}$/min | 900, 25 | | | | | |
| Main crystal phase | low quartz | low quartz | low quartz | low quartz | low quartz | cristobalite |
| Further crystal phases | Li$_2$SiO$_3$; Li$_3$PO$_4$; Li$_2$Si$_2$O$_5$; | Li$_2$Si$_2$O$_5$; Li$_3$PO$_4$ | Li$_2$Si$_2$O$_5$; Li$_3$PO$_4$ | Li$_2$Si$_2$O$_5$; Ca$_2$Al$_2$SiO$_7$ | Li$_2$Si$_2$O$_5$; Ca(PO$_4$)$_3$F | low quartz; Li$_2$Si$_2$O$_5$; Li$_3$PO$_4$; tridymite |
| CR value | | 37.1 | | | 80.5 | |
| CTE/$10^{-6}$K$^{-1}$ (100-500° C.) | 15.9 | | 13.7 | | | |

| | Example No. | | | | | |
|---|---|---|---|---|---|---|
| Composition | 19 wt.-% | 20 wt.-% | 21 wt.-% | 22 wt.-% | 23 wt.-% | 24 wt.-% |
| SiO$_2$ | 78.5 | 73.2 | 72.4 | 75.4 | 75.8 | 75.1 |
| Li$_2$O | 7.6 | 7.4 | 7.5 | 7.2 | 6.6 | 6.7 |
| Na$_2$O | 2.2 | — | — | 0.7 | — | — |
| K$_2$O | — | 3.8 | 2.5 | 4.0 | 3.3 | — |
| Cs$_2$O | — | — | — | — | — | 12.1 |
| Rb$_2$O | — | — | — | — | — | — |
| MgO | 3.1 | 2.2 | 1.6 | — | 2.8 | 3.3 |
| CaO | — | 3.8 | — | — | 3.9 | — |
| SrO | — | — | — | — | — | — |
| ZnO | — | — | — | — | 3.4 | — |
| Al$_2$O$_3$ | 3.9 | 5.8 | 2.3 | 4.3 | — | — |
| La$_2$O$_3$ | — | — | — | — | — | — |
| B$_2$O$_3$ | — | — | — | 3.6 | — | — |
| Y$_2$O$_3$ | — | — | — | — | — | — |
| Ga$_2$O$_3$ | — | — | — | — | — | — |
| In$_2$O$_3$ | — | — | — | — | — | — |
| ZrO$_2$ | — | — | 10.2 | — | — | — |
| TiO$_2$ | — | — | — | — | — | — |
| SnO$_2$ | | | | | | |
| CeO$_2$ | — | — | — | — | — | — |
| GeO$_2$ | | | | | | |
| V$_2$O$_5$ | | | | | | |
| Ta$_2$O$_5$ | | | | | | |
| Nb$_2$O$_5$ | | | | | | |

TABLE I-continued

| | | | | | | |
|---|---|---|---|---|---|---|
| $P_2O_5$ | 4.7 | 3.8 | 3.5 | 4.8 | 4.2 | 2.8 |
| $MoO_3$ | | | | | | |
| $WO_3$ | | | | | | |
| F | — | — | — | — | — | — |
| $T_g/°C.$ | 497 | 511 | 567 | 497 | 492 | 518 |
| $T_s/°C., t_s/min$ | 1650, 120 | 1650, 60 | 1650, 60 | 1650, 120 | 1650, 120 | 1650, 60 |
| $T_{Kb}/°C., t_{Kb}/min$ | 520, 10 | 530, 10 | 590, 10 | 510, 10 | 510, 10 | 540, 10 |
| $T_c/°C., t_c/min$ | 740, 30 | 800, 15 | 850, 10 | 830, 30 | 820, 15 | 830, 15 |
| $T_{Sinter}/°C., t_{Sinter}/min$ | | | | | | |
| $T_{Press}/°C., t_{Press}/min$ | | | | | | |
| Main crystal phase | cristobalite | cristobalite | cristobalite | cristobalite | low quartz | cristobalite |
| Further crystal phases | low quartz; $Li_2Si_2O_5$; $Li_3PO_4$ | high quartz; $Li_2Si_2O_5$; $Li_3PO_4$ | $Li_3PO_4$ | low quartz; $Li_2Si_2O_5$; $Li_3PO_4$ | cristobalite; $Li_2Si_2O_5$; $Li_3PO_4$; diopside | $Li_2Si_2O_5$; $Li_3PO_4$; $Li_2SiO_3$; tridymite |
| CR value | | | 92.8 | 91 | | |
| $CTE/10^{-6}K^{-1}$ (100-500° C.) | | | | | | 15.9 |

| | Example No. | | | | | |
|---|---|---|---|---|---|---|
| Composition | 25 | 26 | 27 | 28 | 29 | 30 |
| $SiO_2$ | 79.7 | 74.2 | 74.2 | 74.2 | 74.2 | 79.2 |
| $Li_2O$ | 4.0 | 5.0 | 5.0 | 5.0 | 5.0 | 5.0 |
| $Na_2O$ | 1.0 | 1.0 | 1.0 | 1.0 | 1.0 | 1.0 |
| $K_2O$ | 2.7 | 2.7 | 2.7 | 2.7 | 2.7 | 2.7 |
| $Cs_2O$ | — | — | — | — | — | — |
| $Rb_2O$ | — | — | — | — | — | — |
| MgO | 3.0 | 6.0 | 6.0 | 6.0 | 6.0 | 3.0 |
| CaO | 2.5 | — | — | — | — | — |
| SrO | — | — | — | — | — | — |
| ZnO | — | — | — | — | — | — |
| $Al_2O_3$ | 3.0 | 3.0 | 3.0 | 3.0 | 3.0 | 3.0 |
| $La_2O_3$ | — | — | — | — | — | — |
| $B_2O_3$ | — | — | — | — | — | — |
| $Y_2O_3$ | — | — | — | — | — | — |
| $Ga_2O_3$ | — | — | — | — | — | — |
| $In_2O_3$ | — | — | — | — | — | — |
| $ZrO_2$ | — | — | — | — | — | — |
| $TiO_2$ | — | — | — | 4.0 | — | — |
| $SnO_2$ | — | — | — | — | — | 2.0 |
| $CeO_2$ | — | — | — | — | — | — |
| $GeO_2$ | — | — | — | — | — | — |
| $V_2O_5$ | — | — | — | — | — | — |
| $Ta_2O_5$ | — | — | 4.0 | — | — | — |
| $Nb_2O_5$ | — | — | — | — | 4.0 | — |
| $P_2O_5$ | 4.1 | 4.1 | 4.1 | 4.1 | 4.1 | 4.1 |
| $MoO_3$ | — | 4.0 | — | — | — | — |
| $WO_3$ | — | — | — | — | — | — |
| F | — | — | — | — | — | — |
| $T_g/°C.$ | 570 | 547.5 | 550 | 550 | 554 | 551 |
| $T_s/°C., t_s/min$ | 1690, 60 | 1680, 60 | 1680, 60 | 1680, 60 | 1680, 60 | 1680, 60 |
| $T_{Kb}/°C., t_{Kb}/min$ | | 570, 10 | 570, 70 | 550, 10 | 570, 10 | 570, 10 |
| $T_c/°C., t_c/min$ | | 830, 15 | 820, 15 | 810, 15 | 830, 15 | 840, 15 |
| $T_{Sinter}/°C., t_{Sinter}/min$ | 910, 10 | | | | | |
| $T_{Press}/°C., t_{Press}/min$ | | | | | | |
| Main crystal phase | low quartz | low quartz | cristobalite | cristobalite | cristobalite | cristobalite |
| Further crystal phases | $Li_3PO_4$; diopside; cristobalite | cristobalite; $Li_2SiO_3$; $Li_3PO_4$ | low quartz; $Li_3PO_4$ | $Li_3PO_4$; low quartz; $TiO_2$; $MgSiO_3$ | $Li_3PO_4$; low quartz; $Li_2SiO_3$ | $Li_3PO_4$; tridymite |
| CR value | | | | | | |
| $CTE/10^{-6}K^{-1}$ (100-500° C.) | 17.3 | | | | | |

| | Example No. | | | | |
|---|---|---|---|---|---|
| Composition | 31 | 32 | 33 | 34 | 35 |
| $SiO_2$ | 77.0 | 76.1 | 78.3 | 72.2 | 86.0 |
| $Li_2O$ | 9.0 | 6.2 | 6.6 | 7.5 | 9.0 |
| $Na_2O$ | 2.2 | — | — | — | — |
| $K_2O$ | — | 3.2 | 3.0 | 3.2 | — |
| $Cs_2O$ | — | — | — | — | — |
| $Rb_2O$ | — | — | — | — | — |
| MgO | 3.1 | 1.6 | 1.5 | 1.8 | — |
| CaO | — | 2.9 | 2.8 | 1.9 | — |
| SrO | — | — | — | — | — |
| ZnO | — | — | — | — | — |
| $Al_2O_3$ | 3.9 | 6.8 | 3.0 | 3.8 | — |
| $La_2O_3$ | — | — | — | — | — |

TABLE I-continued

| Component | | | | | |
|---|---|---|---|---|---|
| B₂O₃ | — | — | — | — | — |
| Y₂O₃ | — | — | — | — | — |
| Ga₂O₃ | — | — | — | — | — |
| In₂O₃ | — | — | — | — | — |
| ZrO₂ | — | — | 2.0 | — | — |
| TiO₂ | — | — | — | 1.8 | — |
| SnO₂ | — | — | — | — | — |
| CeO₂ | — | — | — | 1.8 | — |
| GeO₂ | — | — | — | 2.3 | — |
| V₂O₅ | — | — | — | — | — |
| Ta₂O₅ | — | — | — | — | — |
| Nb₂O₅ | — | — | — | — | — |
| P₂O₅ | 4.8 | 3.2 | 2.8 | 3.3 | 5.0 |
| MoO₃ | — | — | — | — | — |
| WO₃ | — | — | — | — | — |
| F | — | — | — | | |
| Er₂O₃ | | | | 0.1 | — |
| Tb₄O₇ | | | | 0.3 | — |
| $T_g$/° C. | 483 | 523 | 513 | 494 | 445 |
| $T_s$/° C., $t_s$/min | 1650, 60 | 1640, 90 | 1640, 150 | 1650, 120 | 1700, 60 |
| $T_{Kb}$/° C., $t_{Kb}$/min | 500, 10 | 540, 10 | 530, 10 | 510, 10 | |
| $T_c$/° C., $t_c$/min | 830, 10 | 800, 15 | 820, 15 | 780, 60 | 920, 15 |
| $T_{Sinter}$/° C., $t_{Sinter}$/min | | | | | |
| $T_{Press}$/° C., $t_{Press}$/min | | | | | |
| Main crystal phase | low quartz | cristobalite | low quartz | low quartz | low quartz |
| Further crystal phases | Li₃PO₄; Li₂Si₂O₅ | Li₃PO₄ | Li₂Si₂O₅; Li₃PO₄ | Li₂Si₂O₅; Li₃PO₄ | Li₂Si₂O₅; Li₃PO₄; cristobalite |
| CR value | | | | | |
| CTE/10⁻⁶K⁻¹ (100-500° C.) | | | 16.9 | | |

The invention claimed is:

1. Process for the preparation of a dental restoration in which a glass ceramic which comprises the following components

| Component | wt.-% |
|---|---|
| SiO₂ | 58.0 to 92.0 |
| Li₂O | 2.0 to 10.0 | and comprises SiO₂ as main crystal phase is given the shape of the desired dental restoration, wherein said dental restoration comprises a bridge, inlay, onlay, veneer, abutment, partial crown, crown or facet.

2. Process according to claim 1, wherein the glass ceramic comprises 60.0 to 90.0 wt.-% SiO₂.

3. Process according to claim 1, wherein the glass ceramic comprises 2.8 to 9.0 wt.-% Li₂O.

4. Process according to claim 1, wherein the glass ceramic comprises 0 to 13.0 wt.-% further alkali metal oxide $Me^I_2O$.

5. Process according to claim 1, wherein the glass ceramic comprises 0 to 11.0 wt.-% oxide of divalent elements $Me^{II}O$.

6. Process according to claim 1, wherein the glass ceramic comprises 0 to 10.0 wt.-% oxide of trivalent elements $Me^{III}_2O_3$.

7. Process according to claim 1, wherein the glass ceramic comprises 0 to 21.0 wt.-% further oxide of tetravalent elements $Me^{IV}O_2$.

8. Process according to claim 1, wherein the glass ceramic comprises 0 to 7.0 wt.-% P₂O₅.

9. Process according to claim 1, wherein the glass ceramic comprises 0 to 6.0 wt.-% further oxide of pentavalent elements $Me^V_2O_5$.

10. Process according to claim 1, wherein the glass ceramic comprises 0 to 6.0 wt.-% oxide of hexavalent elements $Me^{VI}O_3$.

11. Process according to claim 1, wherein the glass ceramic comprises 0 to 5.0 wt.-% fluorine.

12. Process according to claim 1, wherein the glass ceramic comprises at least one of the following components in the specified amounts:

| Component | wt.-% |
|---|---|
| $Me^I_2O$ | 0 to 13.0 |
| $Me^{II}O$ | 0 to 11.0 |
| $Me^{III}_2O_3$ | 0 to 10.0 |
| $Me^{IV}O_2$ | 0 to 21.0 |
| P₂O₅ | 0 to 7.0 |
| $Me^V_2O_5$ | 0 to 6.0 |
| $Me^{VI}O_3$ | 0 to 6.0 |
| fluorine | 0 to 5.0. |

13. Process according to claim 1, wherein the glass ceramic comprises low quartz, cristobalite or a mixture thereof as main crystal phase.

14. Process according to claim 1, wherein the glass ceramic comprises 5.0 to 50.0 wt.-% SiO₂ as crystal phase.

15. Process according to claim 1, wherein the glass ceramic comprises lithium phosphate and/or lithium silicate as further crystal phase.

16. Process according to claim 1, wherein the glass ceramic is present in the form of a powder, a frit, a blank or a dental restoration.

17. Process according to claim 1, wherein the glass ceramic is prepared by subjecting a starting glass which comprises the following components

| Component | wt.-% |
|---|---|
| SiO₂ | 58.0 to 92.0 |
| Li₂O | 2.0 to 10.0 | to at least one heat treatment at a temperature of from 700 to 950° C.

18. Process according to claim 17, wherein
(a) powder of the starting glass, optionally after the addition of further components, is pressed to form a powder compact, and
(b) the powder compact is subjected to a heat treatment at a temperature of 700 to 950° C.; or
(a') melt of the starting glass is shaped to form a glass blank, and
(b') the glass blank is subjected to a heat treatment at a temperature of 700 to 900° C.

19. Process according to claim 1, wherein the glass ceramic is given the shape of the desired dental restoration by pressing, sintering or machining.

20. Process for the preparation of a dental restoration in which a starting glass which comprises the following components

| Component | wt.-% |
|---|---|
| $SiO_2$ | 58.0 to 92.0 |
| $Li_2O$ | 2.0 to 10.0 | and comprises nuclei for the crystallization of $SiO_2$ is given the shape of the desired dental restoration, wherein said dental restoration comprises a bridge, inlay, onlay, veneer, abutment, partial crown, crown or facet.

* * * * *